(12) United States Patent
Herman et al.

(10) Patent No.: US 10,198,556 B2
(45) Date of Patent: Feb. 5, 2019

(54) MEDICAMENT COMPILATION AND DISPENSATION SYSTEM

(71) Applicants: Randy Herman, St. Michael, MN (US); Connor Herman, St. Michael, MN (US); Tyler Herman, St. Michael, MN (US)

(72) Inventors: Randy Herman, St. Michael, MN (US); Connor Herman, St. Michael, MN (US); Tyler Herman, St. Michael, MN (US)

( * ) Notice: Subject to any disclaimer, the term of this patent is extended or adjusted under 35 U.S.C. 154(b) by 0 days.

(21) Appl. No.: 14/884,956

(22) Filed: Oct. 16, 2015

(65) Prior Publication Data

US 2016/0162661 A1    Jun. 9, 2016

Related U.S. Application Data

(60) Provisional application No. 62/064,611, filed on Oct. 16, 2014.

(51) Int. Cl.
*A61J 7/02* (2006.01)
*G06F 19/00* (2018.01)
*A61J 7/00* (2006.01)
*A61J 7/04* (2006.01)

(52) U.S. Cl.
CPC ........ *G06F 19/3462* (2013.01); *A61J 7/0084* (2013.01); *A61J 7/049* (2015.05); *A61J 7/0454* (2015.05); *A61J 7/0481* (2013.01); *G06F 19/00* (2013.01)

(58) Field of Classification Search
USPC .......................................... 700/243
See application file for complete search history.

(56) References Cited

U.S. PATENT DOCUMENTS

| | | | |
|---|---|---|---|
| 4,444,212 A * | 4/1984 | Ristvedt | G07D 3/128 453/10 |
| 5,713,485 A * | 2/1998 | Liff | G06F 19/3462 221/2 |
| 6,263,259 B1 * | 7/2001 | Bartur | A61J 7/0481 700/236 |
| 6,564,121 B1 * | 5/2003 | Wallace | G06F 19/322 700/231 |
| 8,989,893 B2 * | 3/2015 | Jones | A23G 9/22 221/24 |
| 9,542,534 B1 * | 1/2017 | Ducatt | G06F 19/3462 |
| 9,550,619 B2 * | 1/2017 | Park, IV | B65D 83/0409 |
| 2003/0036683 A1 * | 2/2003 | Kehr | G06F 19/325 600/300 |
| 2003/0183642 A1 * | 10/2003 | Kempker, Sr. | A61J 7/0084 221/2 |
| 2005/0240305 A1 * | 10/2005 | Bogash | G06F 19/3462 700/242 |
| 2006/0058724 A1 * | 3/2006 | Handfield | A61J 7/0084 604/20 |

(Continued)

*Primary Examiner* — Timothy R Waggoner
(74) *Attorney, Agent, or Firm* — Briggs and Morgan, P.A.; Daniel A. Rosenberg

(57) ABSTRACT

The invention relates to a medicament dispensing device and system. In particular, the invention relates to a system having multiple containers capable of dispensing multiple medicaments. A center dispensing mechanism then actuates the containers release tray based on prscribed computer controlled settings.

22 Claims, 28 Drawing Sheets

(56) References Cited

U.S. PATENT DOCUMENTS

| | | | |
|---|---|---|---|
| 2006/0163271 A1* | 7/2006 | Hatsuno | B65B 5/103 221/112 |
| 2006/0266763 A1* | 11/2006 | Svabo Bech | G07F 11/16 221/83 |
| 2007/0023444 A1* | 2/2007 | Holloway | A61J 1/03 221/7 |
| 2009/0105876 A1* | 4/2009 | Simpson | A61J 7/0084 700/242 |
| 2009/0281657 A1* | 11/2009 | Gak | A61J 7/0481 700/242 |
| 2010/0140287 A1* | 6/2010 | Richardson | B65D 83/04 221/186 |
| 2010/0184861 A1* | 7/2010 | Politi | A61J 3/10 514/570 |
| 2011/0178634 A1* | 7/2011 | Yuyama | B65B 5/103 700/232 |
| 2012/0204522 A1* | 8/2012 | Kondo | B65B 1/16 53/551 |
| 2014/0214200 A1* | 7/2014 | Chrusciel | G06F 19/3462 700/237 |
| 2014/0244033 A1* | 8/2014 | Ucer | A61J 7/0481 700/237 |

* cited by examiner

| Home | | | | 12:34 PM | | | August 11, 2014 | |
|---|---|---|---|---|---|---|---|---|
| Container # | Medication Type | Description | Dosage | Dispense Amount | Alarm Time | Dispense Time | Relative Notification | Amount Left | Days Left |
| 1 | Ibuprofen | For aches and pains | 2 every 4 hours | 2 | 1:01 PM | 1:00PM | 1:30 PM | 24 | 12 |
| | | | | | | | | | |
| | | | | | | | | | |
| | | | | | | | | | |
| | | | | | | | | | |
| | | | | | | | | | |
| | | | | | | | | | |
| | | | | | | | | | |
| | | | | | | | | | |

Attendant Sign In

FIG. 13B

| Home | 12:34 PM | August 11, 2014 | Attendant Sign In |

Pharmacy Information:

CVS

Address:
Email:
Phone:

Doctor Information:

Dr. _____
Hospital:
Email:
Phone:

FIG. 13C

| Home | | | | 12:34 PM | | | August 11, 2014 | |
|---|---|---|---|---|---|---|---|---|
| Container # | Medication Type | Description | Dosage | Dispense Amount | Alarm Time | Dispense Time | Relative Notification | Amount Left |
| 1 | Ibuprofen | For aches and pains | 2 every 4 hours | 2 | 1:01 PM | 1:00PM | 1:30 PM | 24 |
| | | | | | | | | |
| | | | | | | | | |
| | | | | | | | | |
| | | | | | | | | |
| | | | | | | | | |
| | | | | | | | | |
| | | | | | | | | |
| | | | | | | | | |
| | | | | | | | | |
| | | | | | | EDIT | Sign Out | |

August 11, 2014
12:34 PM
Home
Sign Out
EDIT

Doctor Information:
Dr. _____
Hospital:
Email:
Phone:

Pharmacy Information:
CVS
Address:
Email:
Phone:

Pharmacy Information:

Name:
Date of Birth:
Illnesses:
Blood Type:

August 11, 2014
12:34 PM
Home
Sign Out
EDIT

| Home | | 12:34 PM | August 11, 2014 |
|---|---|---|---|

Activity Log

| Time | Date | Description |
|---|---|---|
| 12:34 Pm | 8/11/2014 | Dropped extra pill from container 1. |
| 1:00 Pm | 8/11/2014 | 2 pills dispensed from container 1 into bin |
| 1:10 Pm | 8/11/2014 | Alarm shutoff. Pills taken. |
| 4:00 Pm | 8/11/2014 | Machine opened for refill by Dr. SoandSo |
| 4:15 Pm | 8/11/2014 | Machine closed |
| | | |
| | | |
| | | |

Sign Out

MEDICAMENT COMPILATION AND DISPENSATION SYSTEM

RELATED APPLICATIONS

The present application claims priority to and incorporates by reference U.S. Provisional Patent No. 62/064,611 filed on Oct. 16, 2014.

BACKGROUND

The invention relates to a medicament dispensing device and system. In particular, the invention relates to a system having multiple containers capable of dispensing multiple medicaments. A center dispensing mechanism then actuates the containers release tray based on prescribed computer controlled settings.

Many patients are required to take different combinations and amounts of medicaments at different times throughout the day. Compliance with such complicated dosage regimens is often challenging, and failure to follow the regimen can have significant adverse effects on the patient.

This is especially the case with elderly patients, or others that may suffer from impaired mental capacity, judgment, or memory—whether that is a short term condition brought on by the condition being treated or a long term chronic situation. The complicated regiment can be difficult for anyone to follow and a particular challenge for those with the limitations set forth above.

As a result, an improved apparatus and system for the delivery of medicaments is needed.

SUMMARY OF THE INVENTION

The invention is directed to a system for compiling and dispensing medicament dosages to a user or patient. The intended use of the system is to organize pills for persons such as the elderly or those who take many medications and distribute the pills or other dosage forms at a given time for the user's consumption, while regulating the pills the user is taking.

An object of the present invention is such a system that substantially eliminates the problems of the prior art. These and other objects of the present invention will become apparent to those skilled in the art upon reference to the following specification, drawings, and claims.

BRIEF DESCRIPTION OF THE FIGURES

FIGS. 13A-M are wire frames of the computer display of the device.

DETAILED DESCRIPTION OF THE INVENTION

Figure 1:
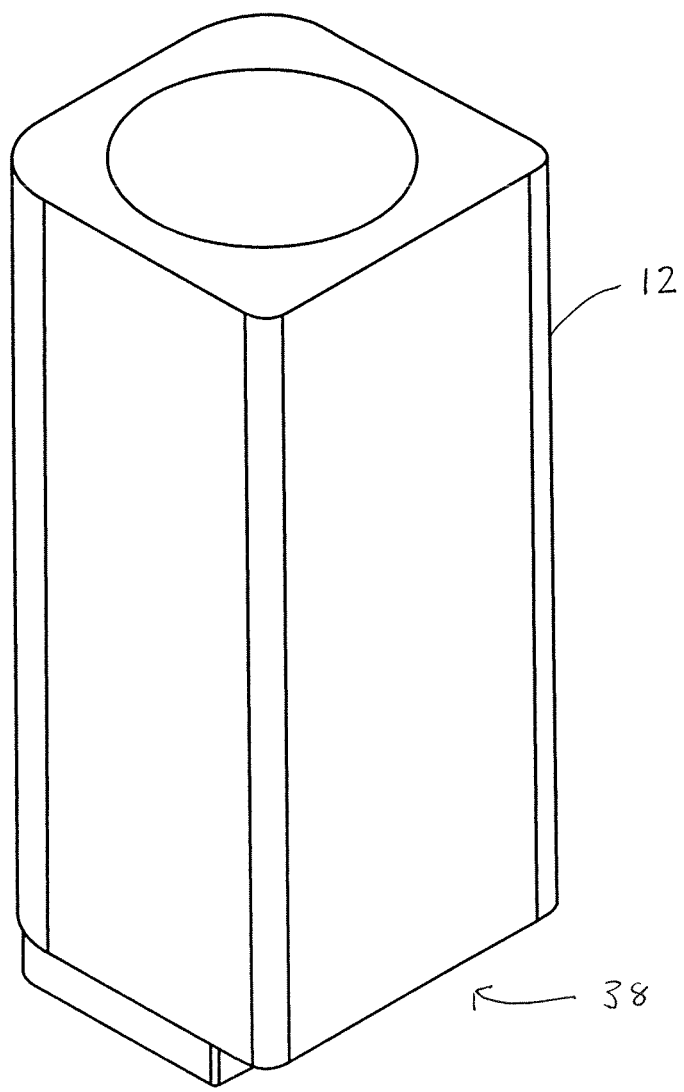
FIG. 1 is a perspective view of a container.

The system generally performs four operations; namely, sorting; releasing; compiling; and dispensing any medicament such as a tablet, pill, capsule, caplet, and the like—which can be a medicine, drug, nutritional or dietary supplement, or vitamin, nutrient, or mineral. The system is designed to deliver a user's prescribed or desired dosage of one or more medicaments, and is particularly adapted to combine a plurality of different medicaments and deliver them to the user at specified amounts and time intervals.

The system may also include a screen that serves as a graphic user interface similar to a cellular phone or tablet computer touchscreen to allow for computerized operation and configuration of the system. The system may be automated or manually operable. The system may include wireless communication elements enabling communication between the dispensation device and the user, family members or other caretakers, a pharmacist, a physician and/or a hospital or medical treatment facility remotely.

The system may be secured from unauthorized access or use, such as by using a lockbox mechanism, passcode, or biometric identifiers, enabling only authorized personnel to add medicaments to the system, and to control the dispensed medicament dosage over time to avoid overusing one or more medicaments.

The system includes a device, having a container, a release assembly, a compiling assembly, and a dispensing assembly, that distributes items in various dosage forms to a receptacle from which the user can obtain the medicament dosage.

The container includes a sorting mechanism to ensure that one unit of the medicament is ready for dispensation at a time, while holding an entire prescription's worth of medicament in the body of the container. The sorting mechanism may be a generally spiral "tornado" structure, a baffle system, or other internal structure that results in one unit of the medicament being positioned to be dispensed at any given time.

The container is coupled to a release assembly to facilitate the controlled release of one unit of the medicament. The release assembly may be any mechanism which can be controlled to release the medicament at a particular time or interval of time. The release mechanism may be a sliding mechanism, a spring-loaded mechanism, a rotating geared mechanism, a magnetically controlled mechanism, and the like.

The medicament unit is released into a compiling and dispensing assembly which includes a receptacle, such as a tray or cup, for collecting medicament units once they are released from the container. The receptacle may be gravity-fed by a sloping path between the container/release assembly and the receptacle. Alternatively, the medicament units may be mechanically fed into the receptacle. The receptacle is secured within the device such that it cannot be removed prior to a pre-determined dispensation time.

Once the medicament units are compiled in the receptacle according to the dosage, the receptacle dispenses the medicament dosage to the user at the appropriate time by automatically sliding the receptacle away from the device so that the dosage units are accessible to the user. Alternatively, the device may alert the user that a dosage is ready to be dispensed (for example by emitting an alarm or sending a signal to a remote wireless device), and the user can manually slide the receptacle away from the device to obtain the medicament dosage. Once the medicaments are removed from the receptacle, it may be slid back into the device, ready to receive the next medicament dosage.

Each element of the device may be coupled to a communication system to indicate proper functioning or to warn of any malfunctions. The communication system may be shared by any number of entities, so that a patient's use of the device to obtain the proper dosage of medicaments at the proper time can be closely monitored. For example, if the patient does not take the prescribed dosage at the correct time, the device may alert a physician or family member that the patient has not complied with the dosage instructions. The patient may also receive a notification on a cellular phone or other device to remind them to take their medication.

The device is programmed to obtain the correct combination of medicament units, in the correct amounts, and dispense the dosage at the correct time.

The device may also be programmed to require the user to take certain steps prior to dispensing the medication. For example, if a particular medicament should be taken with food, the device may first ask the user to confirm that they have eaten before the medicaments are dispensed. If the medicament should be taken on an empty stomach, the device may send the user a pre-dispensation notification to not consume anything for a period of time before the medicaments are dispensed.

The device may also alert the user or others that a particular medicament will need to be refilled soon, and may send the doctor or pharmacy a prescription refill request. The user then may take the device to the doctor or pharmacy to be refilled so that the dosage regimen may continue uninterrupted.

The device may include one container/release assembly, but in a preferred embodiment, the device includes at least two container/release assemblies that are coupled to the compiling/dispensing assembly to provide the user with the appropriate dosage of at least two different medicaments. Other embodiments include 3, 4, 5, 6, or even more container/release assemblies in the device. Of course, each container need not be filled, so for example, a 4-container device could be used to dispense the appropriate dosage of three different medicaments.

Container

One embodiment of the container is shown in FIG. 1. The container 12 is dimensioned to sufficiently hold a full prescription's worth of medicaments, and has an interior structure to collect and sort the medicament so that one unit of the medicament can be released at a time through an exit port 14 positioned at the bottom of the container 12. Other embodiments may include an exit port 14 on a side of the container 12. The container 12 may include a cover 32, or a lockable cover 32, as seen in more detail below.

Release Mechanism

Figure 4:
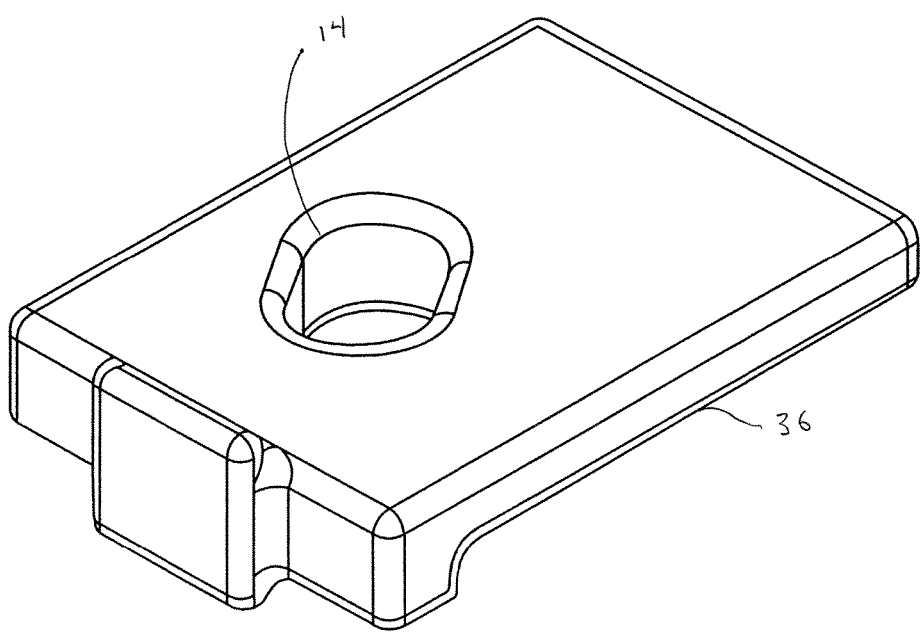
FIG. 4 is a perspective view of a release slide.
Figure 5:
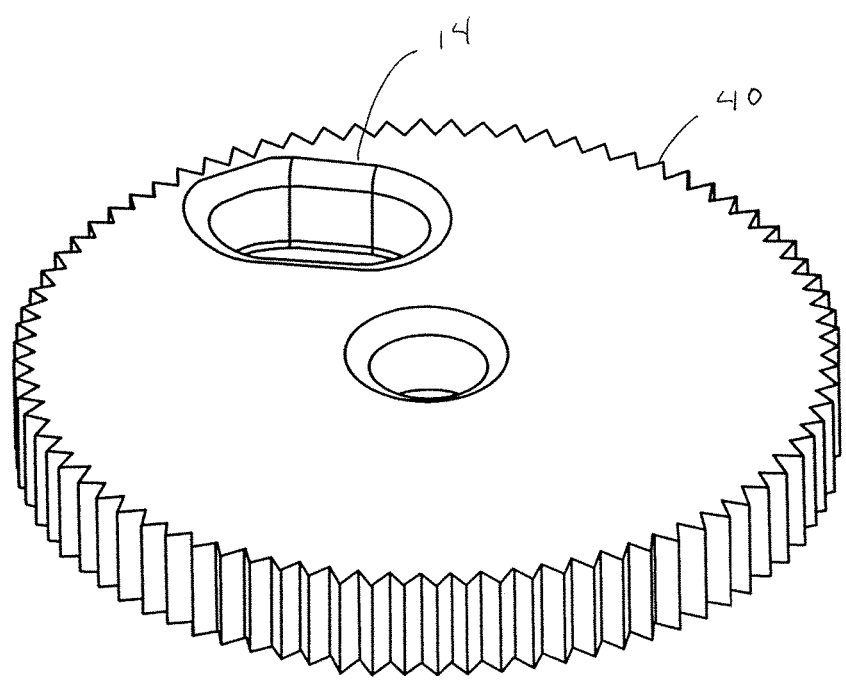
FIG. 5 is a perspective view of a release device.

In certain embodiments, the release mechanism 18 is positioned under the container 12 and can be moved by a computer-controlled motor to align an opening in the release mechanism 18 with the exit port 14 of the container 10 to release one medicament unit. An example of a sliding release mechanism 18 is shown in FIG. 4, and an example of a rotating release mechanism 18 is shown in FIG. 5.

Frame

Figure 7:
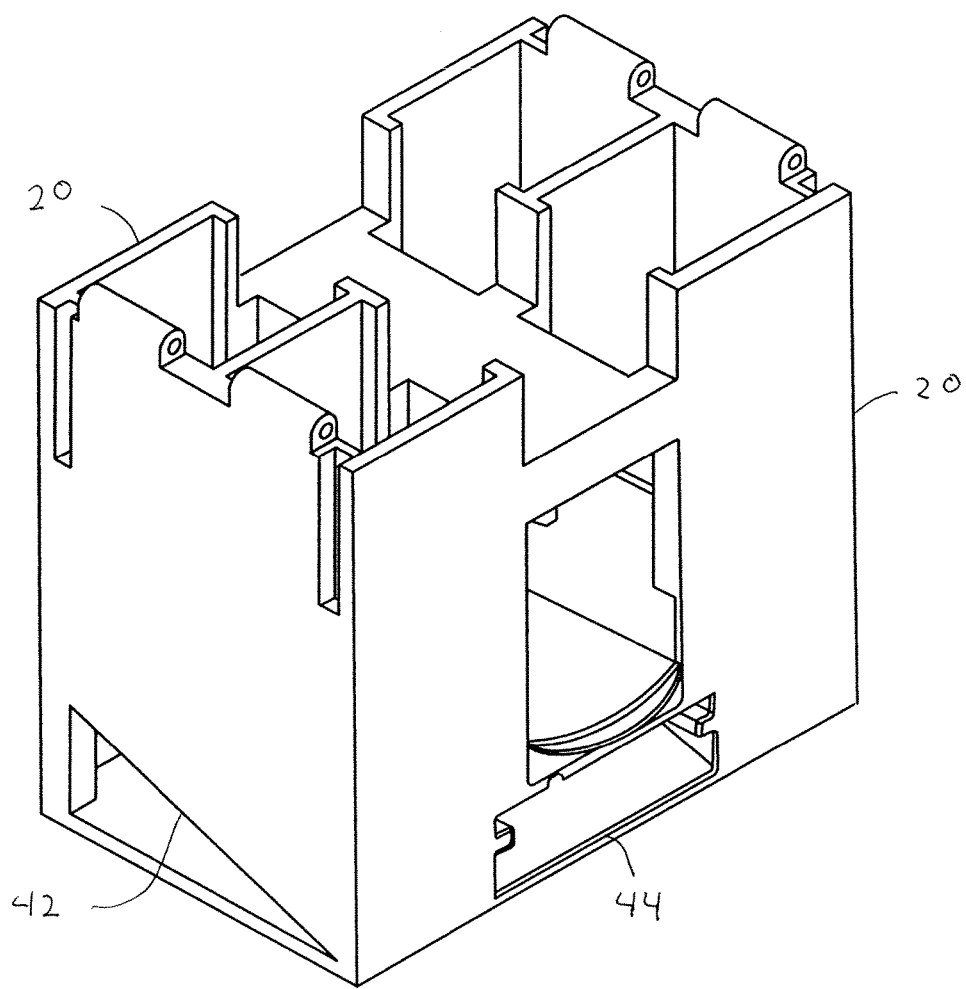
FIG. 7 is a perspective view of a frame.

The interior structure of one embodiment of the device includes a frame 20 for receiving four container/release assemblies, as seen in FIG. 7. This embodiment of the frame 20 includes a sloping pathway to compile medicament units into the dispensing receptacle 22. Other frames 20 for receiving more container/release assemblies are contemplated by the invention. The frames 20 can be housed in a case 26, as will be shown in greater detail below.

A different embodiment of a frame 20 for supporting six containers 12 is shown in FIG. 8. This is a circular frame 20 which also uses sloping pathways to compile medicament units into the receptacle 22.

Tray/Receptacle

Figure 9:
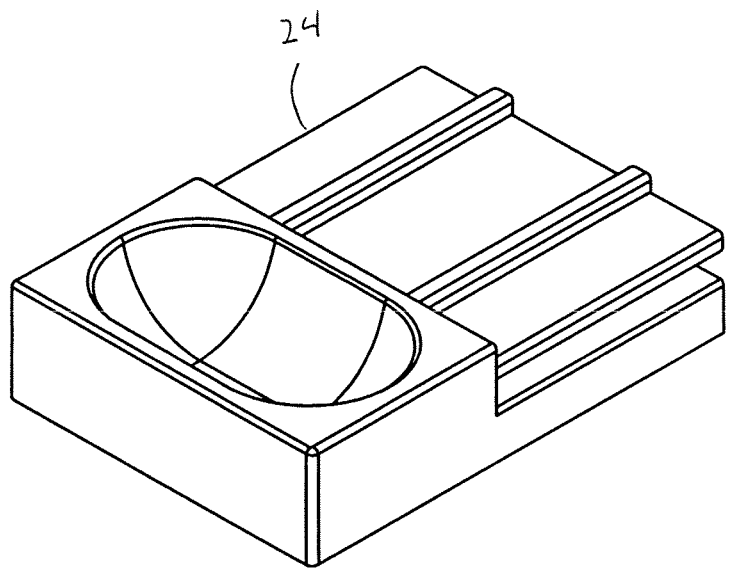
FIG. 9 is a perspective view of a tray.
Figure 10:
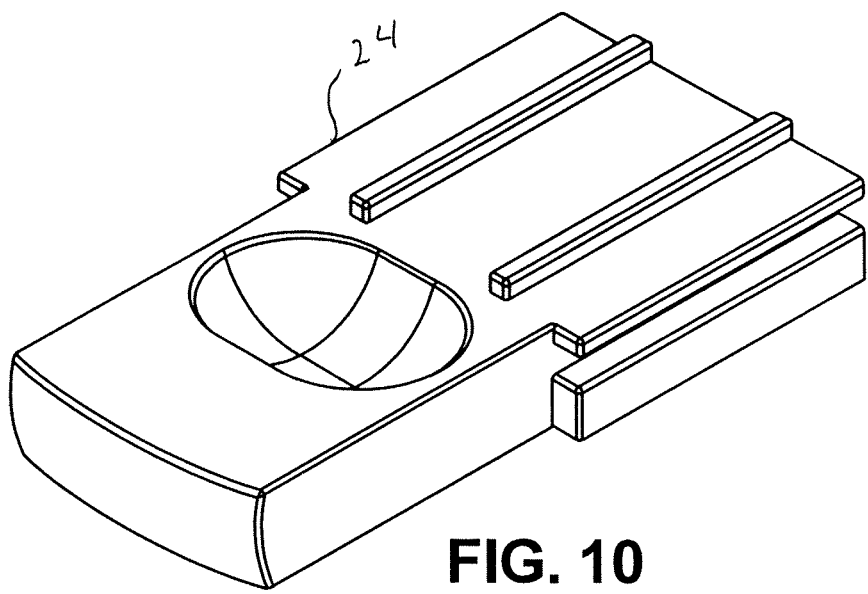
FIG. 10 is a perspective view of the tray.

Embodiments of the receptacle 22 for receiving and dispensing the medicament dosage are shown in FIGS. 9 and 10. The trays 24 shown are designed to sit flush with outer wall of the device until a predetermined time to open, then slide out or can be slid out for retrieval of dispensed medicaments.

Case

Figure 11:
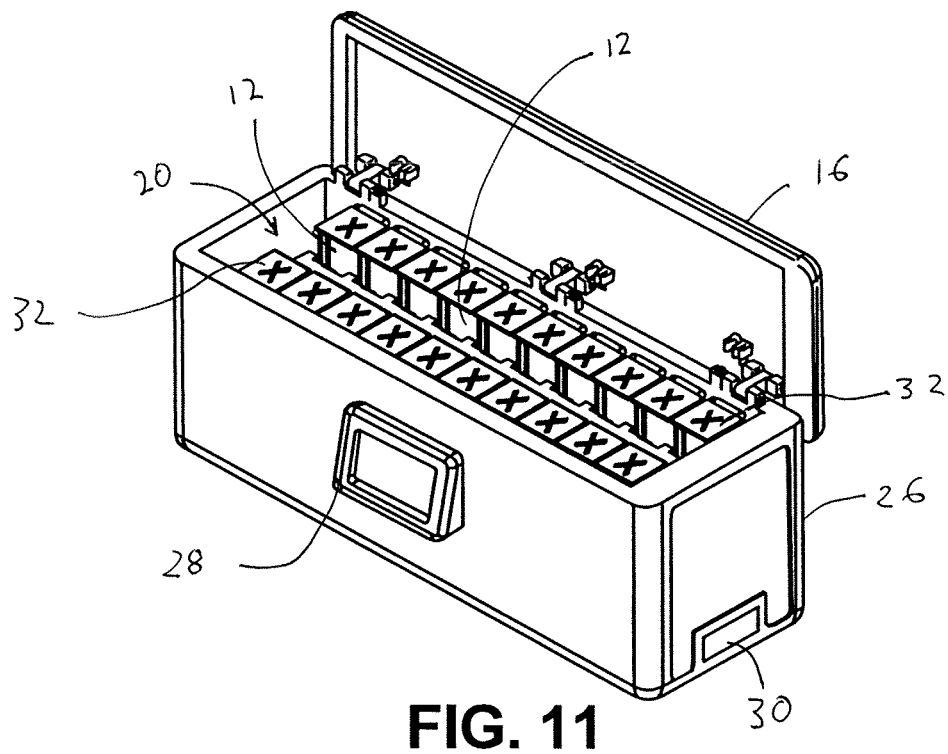
FIG. 11 is a perspective view of the medicament dispensing device.
Figure 12:
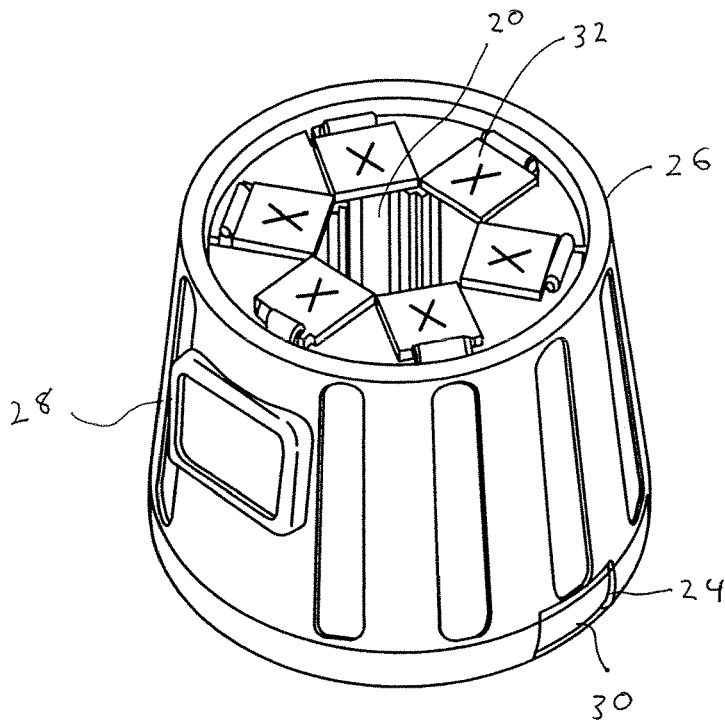
FIG. 12 is a perspective view of the medicament dispensing device.

The containers 12, frame 20 and tray 24 may be housed in a case 26, as shown in the embodiments of FIGS. 11 and 12. The case 26 includes the location of the user interface 28 described above, and includes an opening 30 through which the tray 24 or other receptacle may be easily slid into an open and a shut position either automatically or by the user. The case 26 may be integral with or separate from the frame 20. As seen in these embodiments, the container 12 includes a cover 32 (marked with an "X" in the figures) which may be locked once the container 12 has been filled with the medicament units. The entire case 26 includes a cover 16, which may also be locked to prevent unauthorized access to the medicaments.

User Interface

As described above, the system includes a user interface similar to a cellular phone or tablet computer touchscreen. As will be understood by those skilled in the art, such an interface allows for many levels of communication between the device and the user, and can be used to list the medicaments contained in the device, the list of alarms, pharmacy and doctor contact information, a password secured sign-in for the user and others who may need access to the medicament dosage such as a personal attendant, and the like. The interface may include a log of the medicaments dispensed, and the log and other information may be automatically transmitted to a remote location such as a hospital, family member, and the like.

An example of user interfaces is shown in FIGS. 13a-m. Other interfaces and interface sequences are contemplated by this invention.

Network

Figure 14:
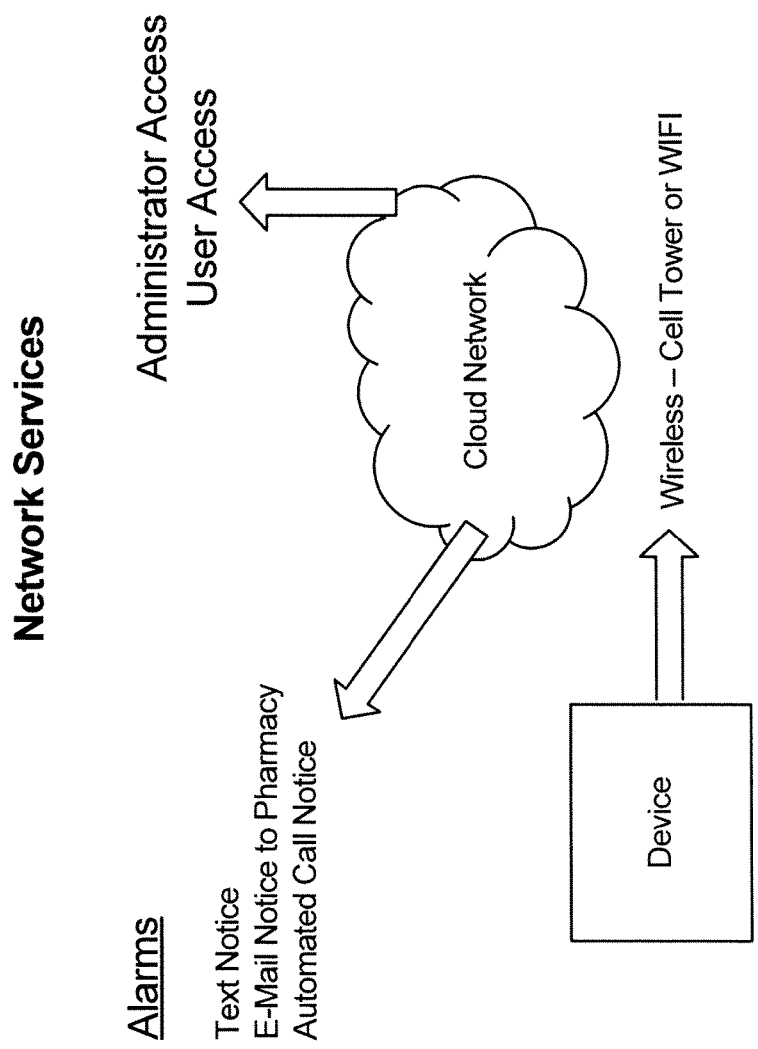
FIG. 14 is a schematic view of the network of the device.

The device may be wirelessly connected to remote receivers or similar devices to monitor compliance with the dosage regimen. One example of a network configuration is shown in FIG. 14. This network configuration may include the device connected to the internet through a cellular tower connection or IEEE 802.xx—WIFE or WI-MAX. The device may have remote access for the user interface as well as for an Administrator interface. The device may send out an alarm or an alarm sequence for various issues or conditions. An example of an alarm sequence may occur when the user has not dispensed medication within a set time period, with a first alarm being sent to the user at, for example 30 minutes, a second alarm being sent to the administrator or a family member at, for example, 45 minutes, and a third alarm being sent to the doctor at, for example, 60 minutes.

Through the network configuration, the device may have the ability to notify a pharmacy of the need for a refill of a particular medicament.

Other network configurations and alarm sequences are contemplated by this invention. Examples of various aspects of the device and system are shown in the following figures, which are intended solely to exemplify certain embodiments of the invention and in no way limit the full scope of the invention.

In particular, FIG. 1 shows a container 12 of the device which comprises a medicament dispensing unit, having an exterior and interior. The center cavity is exposed to allow access to the sorting mechanism in the interior.

Figure 2:
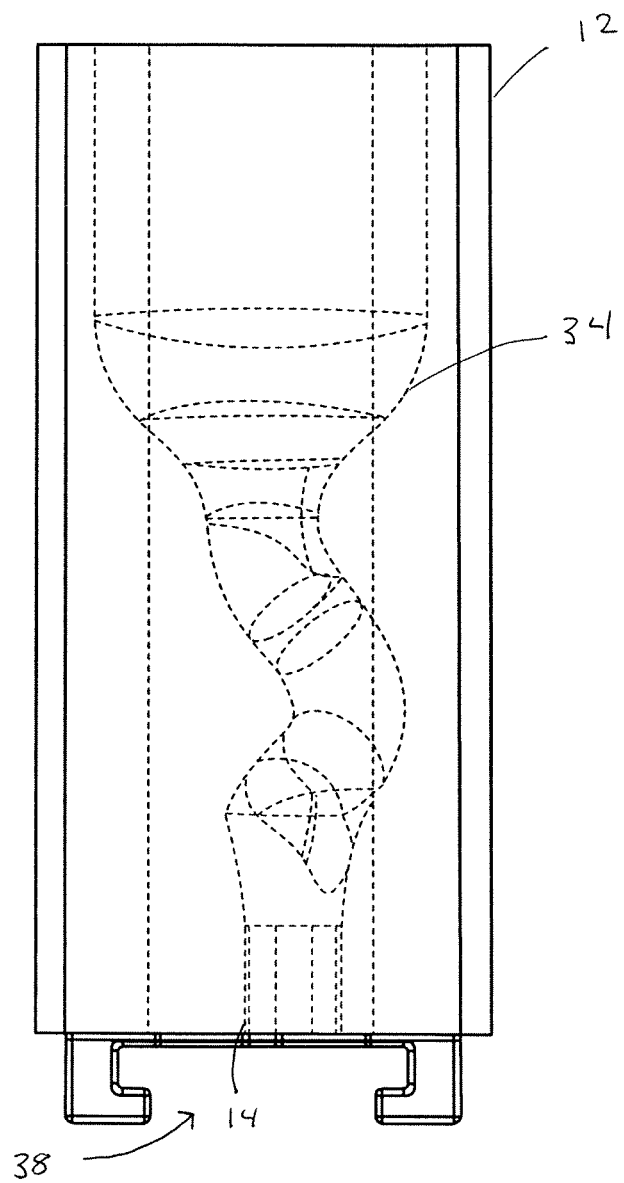
FIG. 2 is a partially transparent perspective view of the container.

FIG. 2 shows in dashed lines the interior of the container 12 in which is located the sorting mechanism 34—comprised of a generally spiral "tornado" structure. The sorting mechanism 34 is wide at the top to accommodate a large number of medicaments, but comprises various narrowing turns and twists that restrict the flow of the medicament such that only the desired number of medicament reach the bottom of the mechanism 34 such that the measured release of medicament matches the desired dose. Most commonly that would be one medicament dose at a time. The medicament is released from the sorting mechanism 34 at the exit port 14 at the bottom of the container 12.

Figure 3:
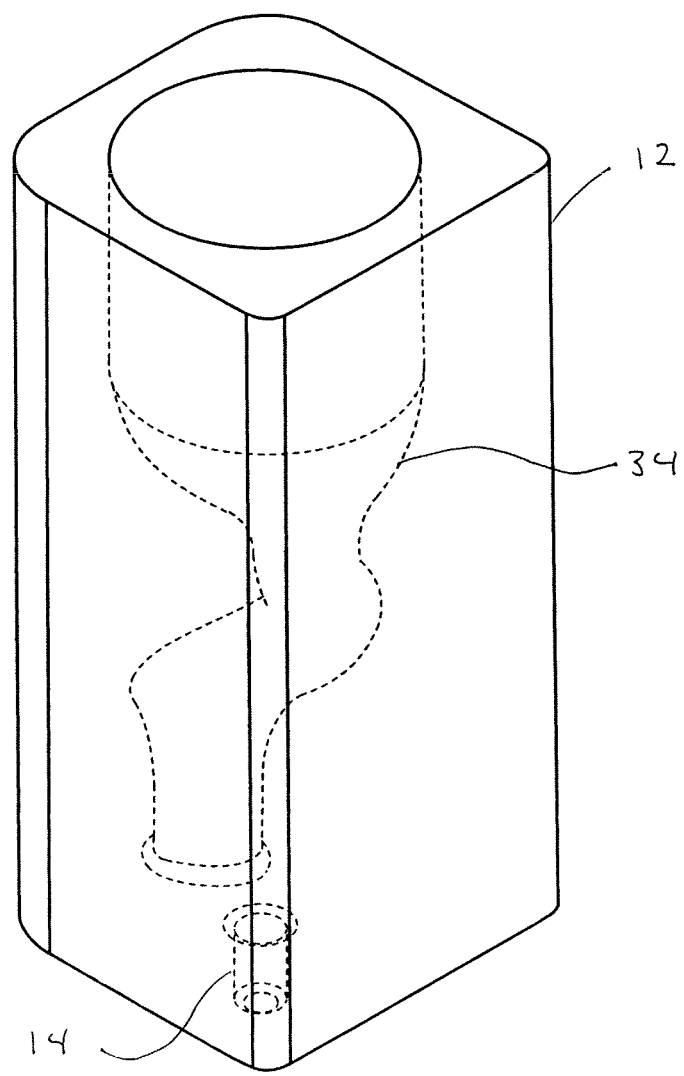
FIG. 3 is a partially transparent perspective view of the container.

FIG. 3 shows container 12 including the exit port 14, which is the final release point from the sorting mechanism 34. The exit port 14 is sized to ensure the release of the proper does. The invention can include a plurality of ports 14 of different sizes that may be exchanged during set up to match the size of the medicament.

Figure 4A:
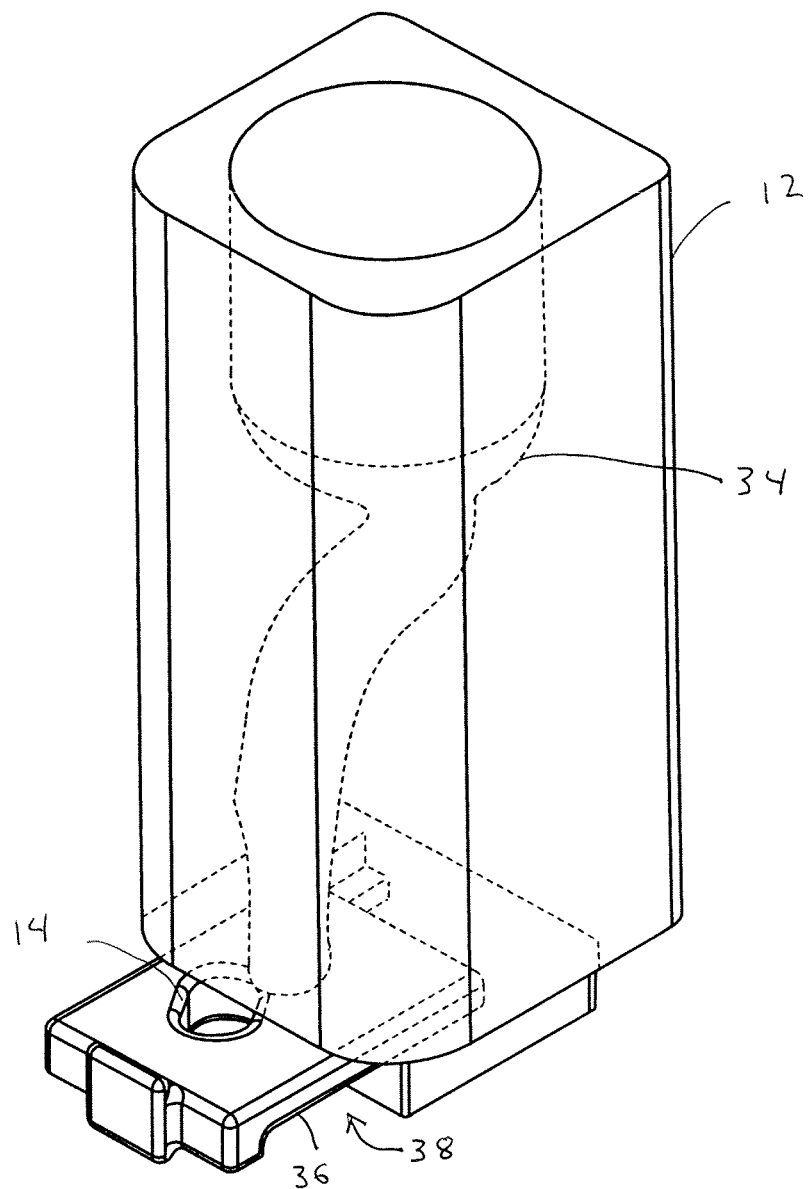
FIG. 4A is a partially transparent perspective view of the container and release slide.

FIG. 4 shows a release slide 36 that fits into a slot at the bottom of the container 12. The release slide 36 can be pulled out by a user at the prescribed time and the proper does of the medicament is in the exit port 14. FIG. 4a shows the release slide 36 partially removed to allow the user to access the medicament. When in this position the bottom of the sorting mechanism 34 is covered by the release slide 36 to ensure that the medicament can only be dispensed into the exit port 14.

FIG. 5 shows an alternative release device 40 that is comprised of a circular gear with teeth that can engage with a driving device to turn the release and move the dose in the exit port 14 to an opening in the container 12 to allow the user to remove the medicament dose. This embodiment of the invention can include a powered driving device to automatically move the release device 40.

Figure 6:
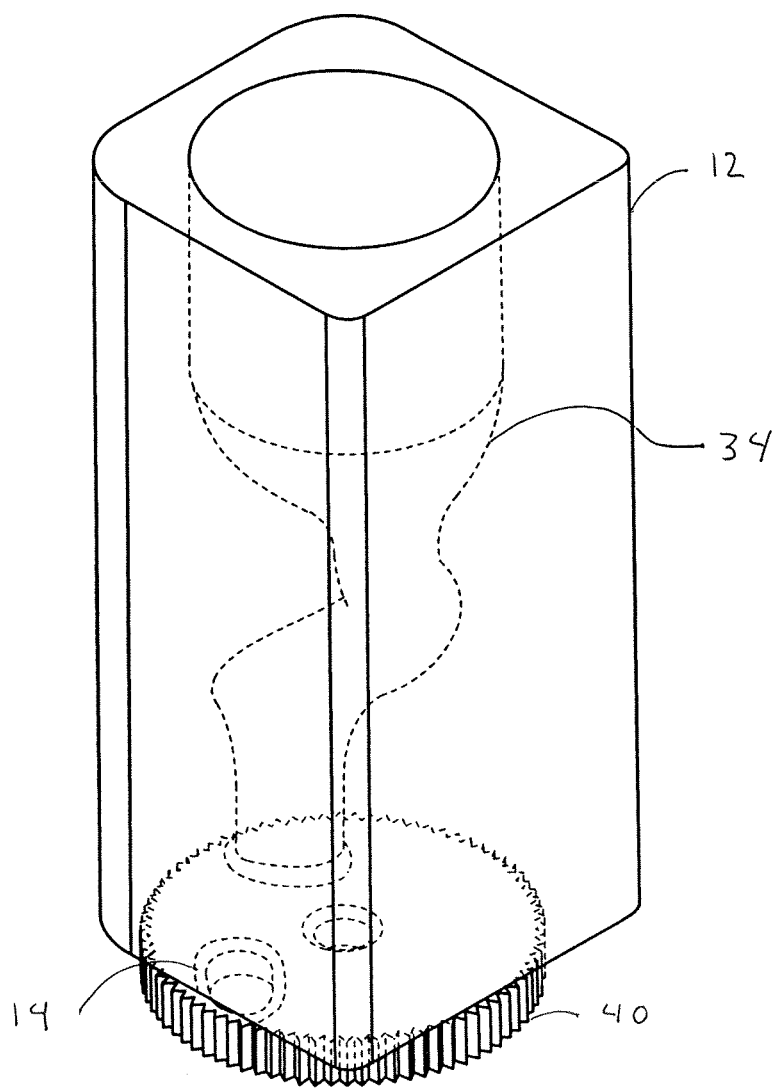
FIG. 6 is a partially transparent perspective view of the container and release device.

FIG. 6 shows the release device 40 of FIG. 5 in combination with the container 12.

FIG. 7 shows a container frame 20, wherein the containers 12 described above can be placed into the frame 20 to provide the ability to dispense multiple medicaments. The bottom of the frame 20 includes a sloping pathway 42 that would lead to a tray 24 having exit ports 14 for each container 12. The tray 24 would fit into the slot 44 at the bottom of the frame 20.

Figure 8A:
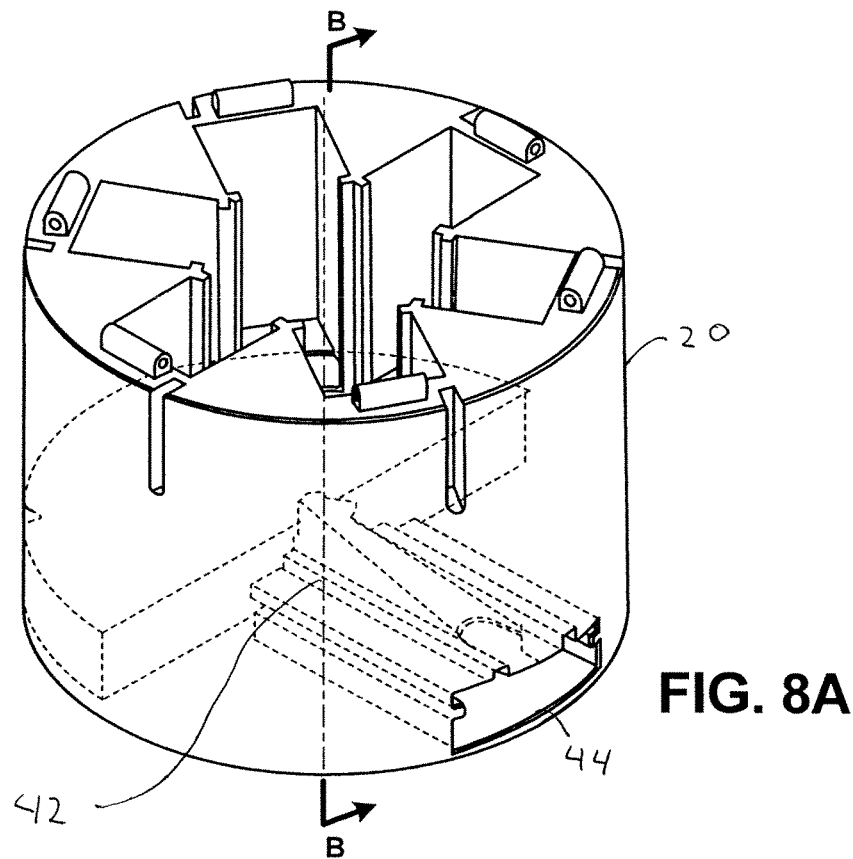
FIG. 8A is a partially transparent perspective view of the frame.
Figure 8B:
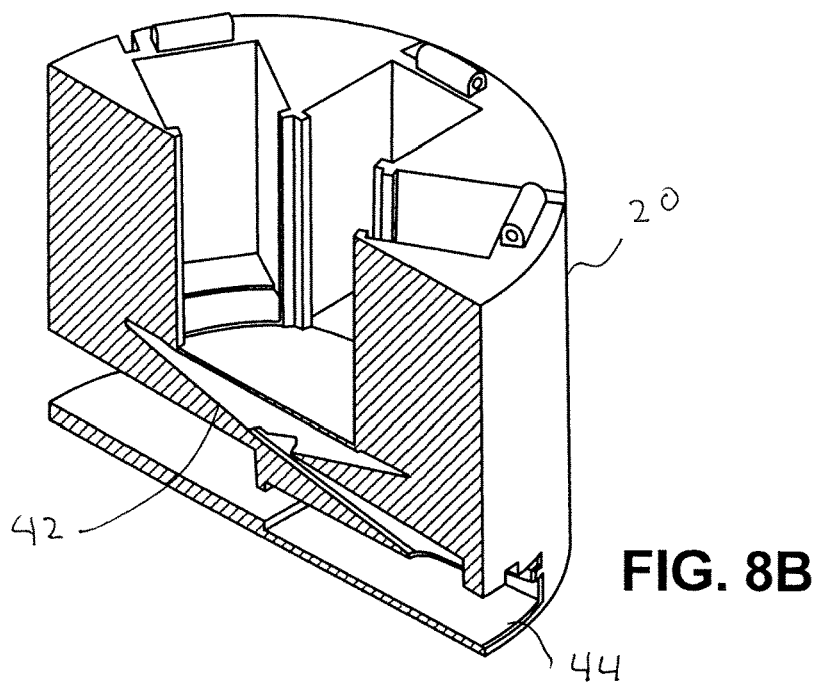
FIG. 8B is a cross sectional perspective view of the frame taken along the line B-B shown in FIG. 8A.

FIGS. 8a and 8b shows an embodiment of the invention having a circular frame 20, which is again designed to receive multiple containers 12, and also includes a sloping pathway 42 leading to an opening 44 that accommodates the tray 24.

FIGS. 9 and 10 show the trays 24 for the rectangular and circular frames 20 (respectively).

Figure 11A:
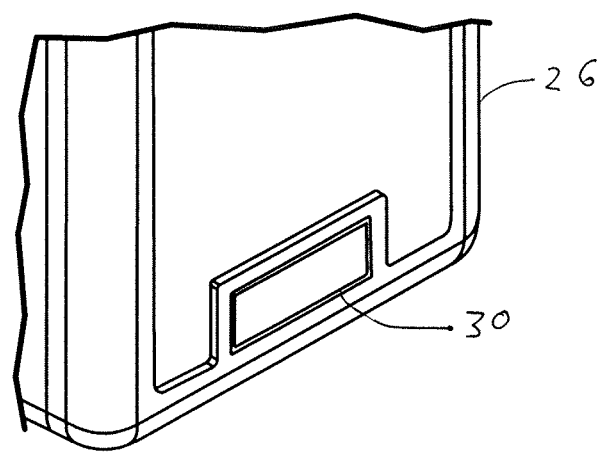
FIG. 11A is a view of a portion of the medicament dispensing device.
Figure 11B:
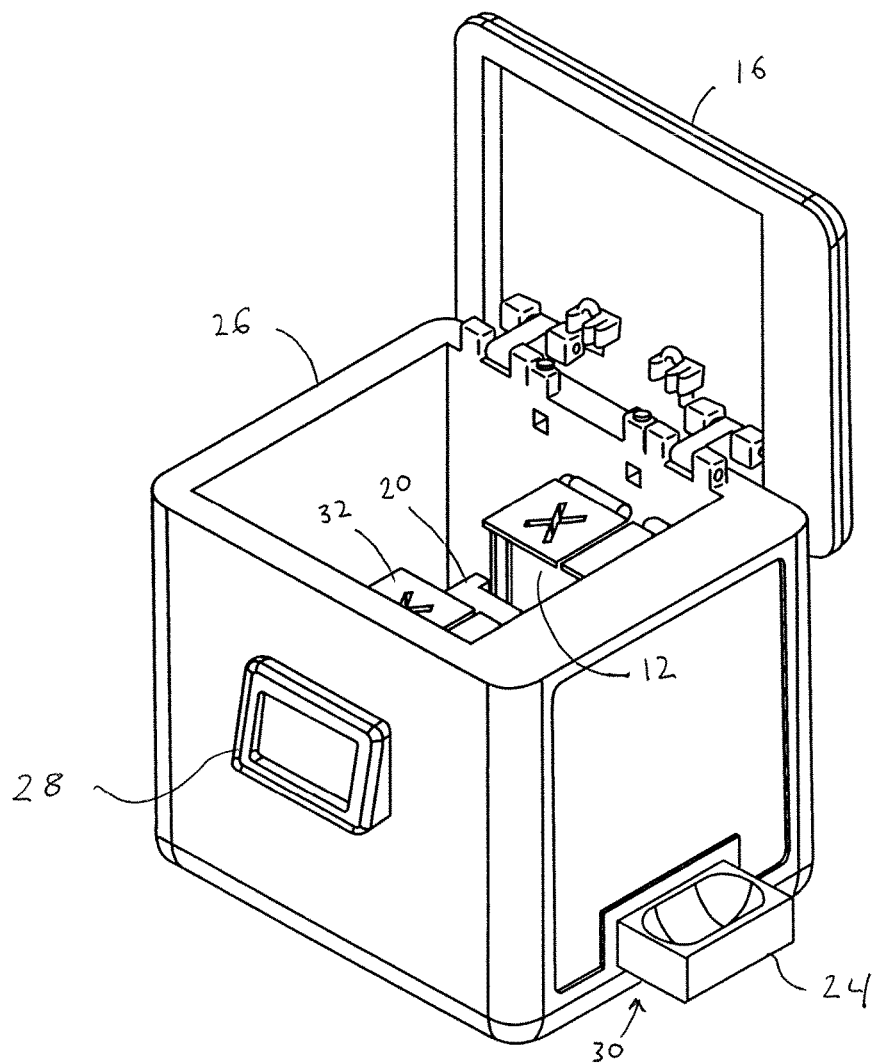
FIG. 11B is a perspective view of the medicament dispensing device.

FIG. 11 shows a case 26 having a rectangular frame 20 therein for storing multiple containers 12 therein. A tray 24 can be inserted into the slot 30 is located at the bottom side of the container 12 (see FIG. 11a). Each container 12 includes a hinged cover 32 (marked with an X). FIG. 11b shows a smaller version of the case 26 and rectangular frame 20 with containers 12 therein and the tray 24 in the open position. The user interface touch screen is also shown.

Figure 12A:
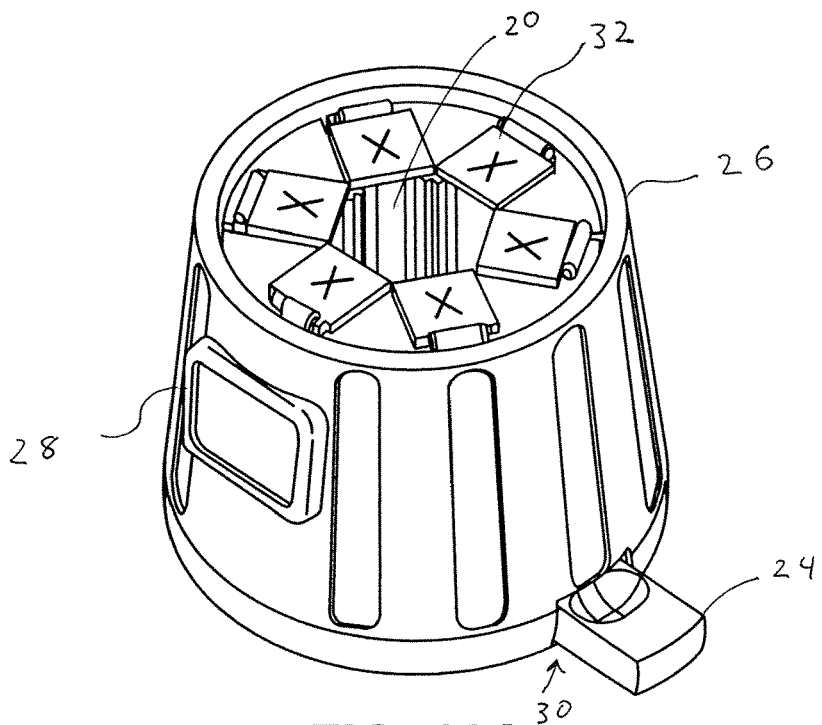
FIG. 12A is a perspective view of the medicament dispensing device.

FIGS. 12 and 12a show the circular case 26, internal frame 20, and containers 12, with the tray 24 in the closed and open position. The touch screen is also shown.

Figure 15:
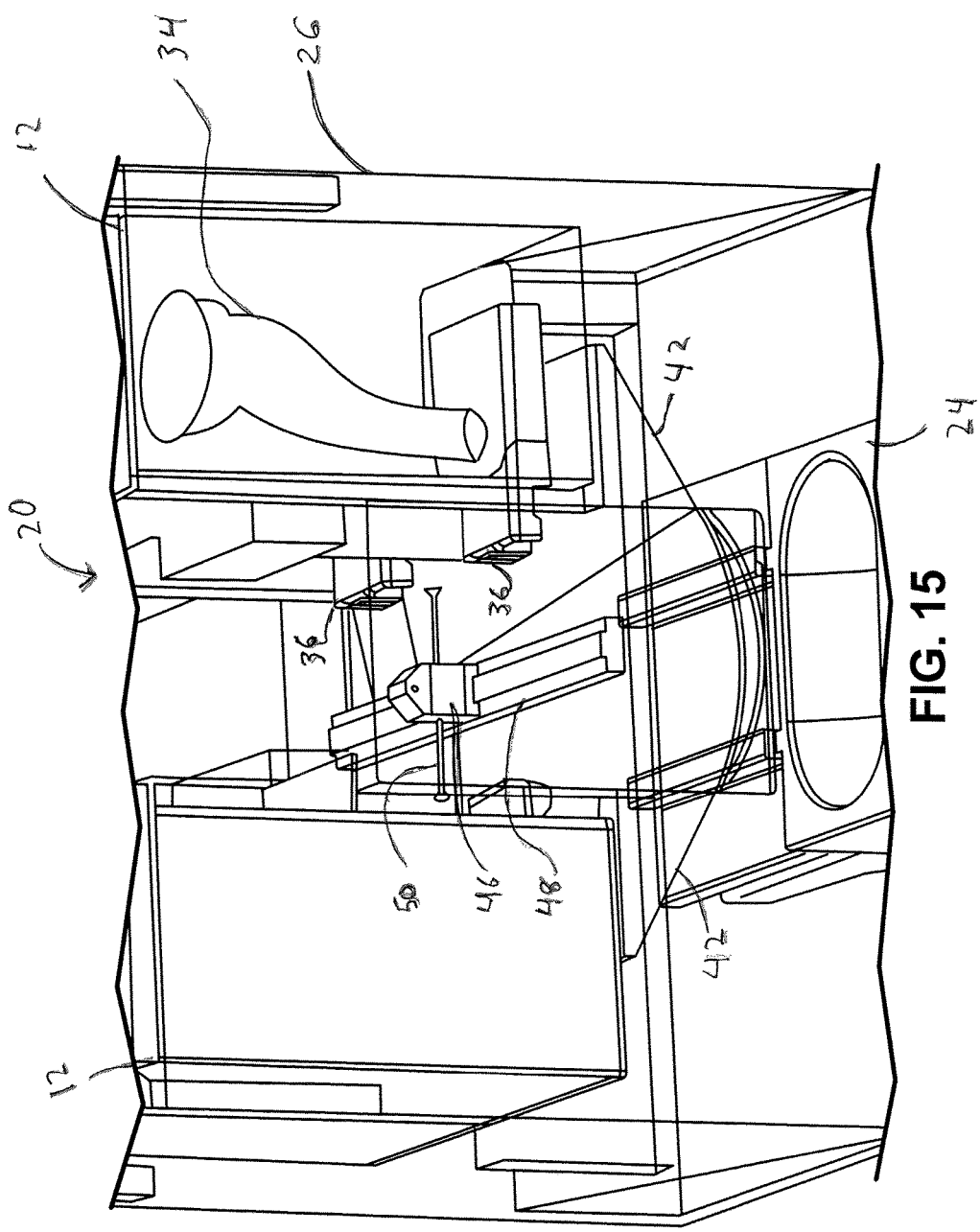
FIG. 15 is a partial perspective view of the frame, containers, and actuating system of the device.

FIG. 15 shows the portion of the system that dispenses medicaments from the multiple container frames 20. In particular, the system utilizes a linear motion system to move an actuator 46 on a rail 48. The rail is 48 mounted in the center of the containers 12 equidistant from the containers 12. The rail 48 includes a raised ridge with tapered sides that mates with a slot on the bottom of the actuator 46. The actuator 46 moves along the rail 48. The actuator 46 further comprises a threaded push rod 50 that when turned moves perpendicular to the rail 48. The actuator 48 spins the push rod 50 which then engages the slide release 36 (see FIG. 4). The slide release 36 is biased into a position that covers the bottom of the spiral sorting mechanism 34. The push rod 50 moves the slide release 36 back so that that the exit port 14 in the center of the slide release 36 aligns with the bottom of the sorting mechanism 34 and allows a dose of medicament to be released onto the sloped pathway 42 which gravity feeds the medicament to the tray 24 (see FIG. 9). The actuator 46 is under computer control and can therefore actuate any combination of container release trays 24 and prescribed by the user through the interface software.

While a linear actuator is described, the actuator can take a variety of other forms, including the use of a belt drive to move the actuator, a stepper motor, gear drives, ball screws, and the like.

The circular container 12 can use a similar dispensing system. In one embodiment, the actuator can rotate rather than mover linearly, but still use the push rod to engage the release trays 24. Alternatively, a series of gears can be used to engage and rotate the release tray 24 shown in FIG. 5.

Figure 13A:
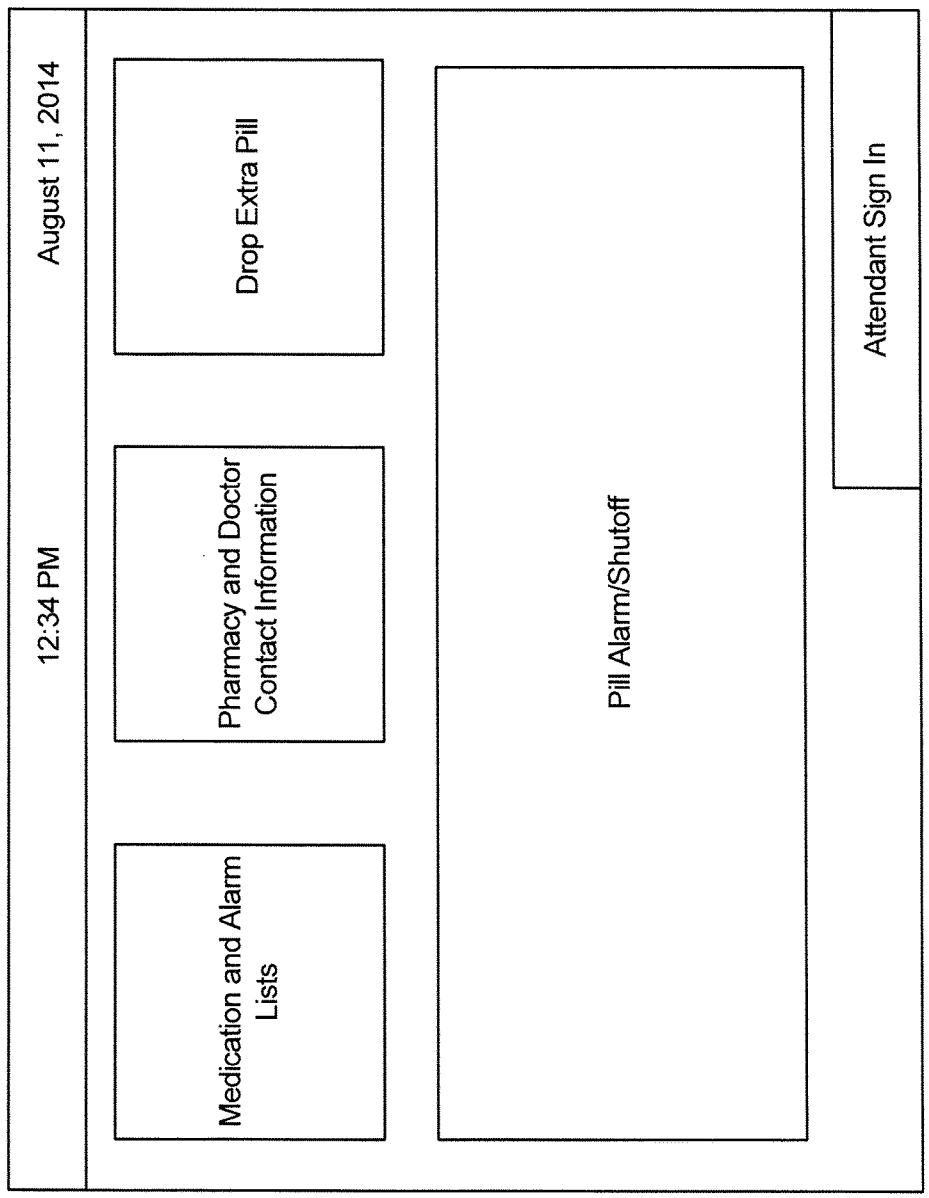

FIGS. 13a-m are wire frames of various user interface touch screens. FIG. 13a shows a screen that includes an alarm shut off feature, which would allow the user to shut off an alarm which indicates that it is time for the user to take a medicament. The screen includes an alarm list pad where the user can view and set alarms, a contact screen that allows the user to view and set emergency or medical contacts, and a tab to dispense additional medicament in case the device does not deliver a dose. There is also a sign in screen to allow for user identification.

FIG. 13b includes a log screen where the device shows activity relating to the dispensing of medicaments. The screen can be accessed from a tab on a home screen or elsewhere.

FIG. 13c shows a contact information screen, which for example can be used to show doctor and pharmacy screens.

Figure 13D:
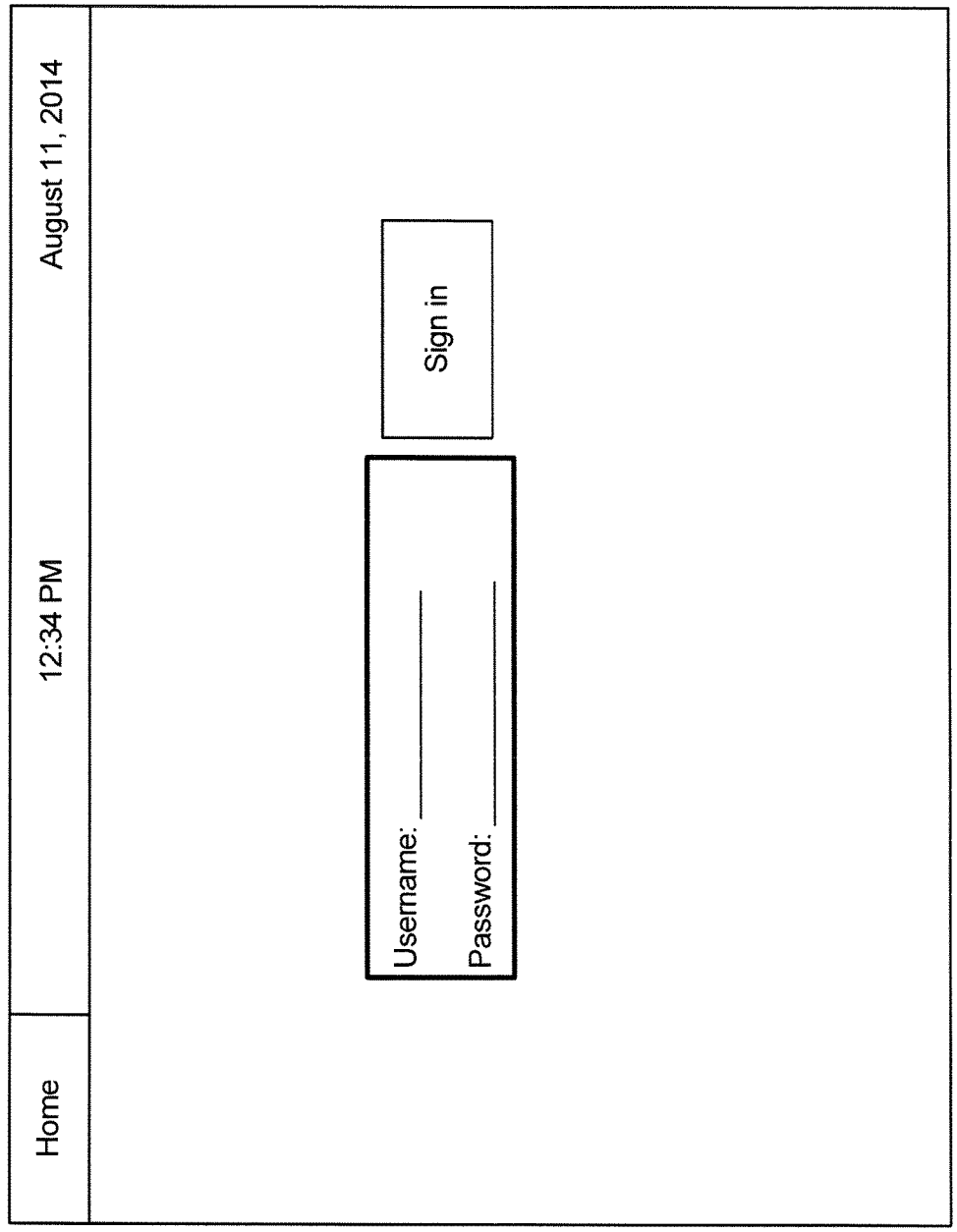

FIG. 13d shows a login screen that requires the user to enter a username and password to access the interface/device.

Figure 13E:
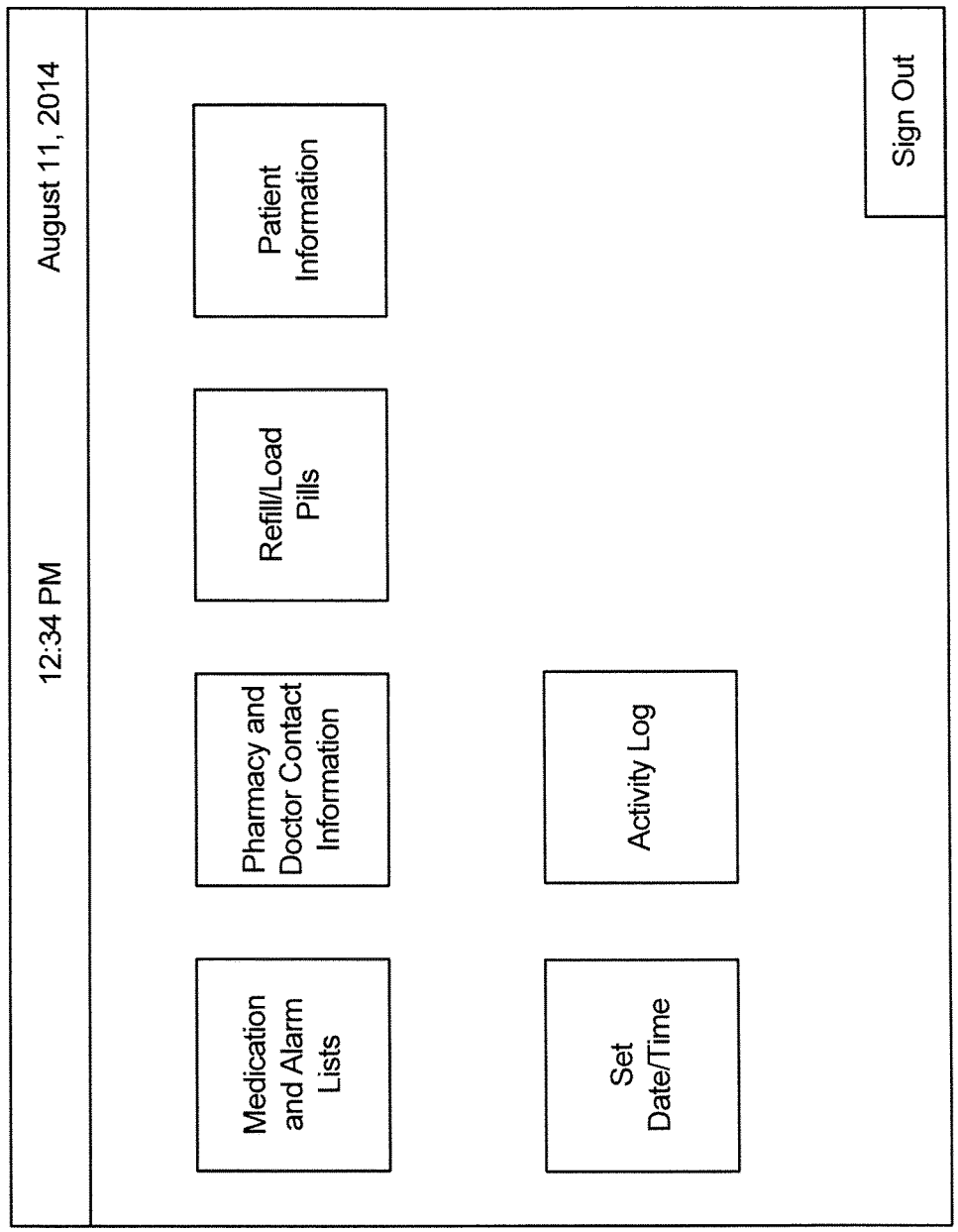

FIG. 13e shows a general/home screen with tabs to access the various screens described herein.

FIG. 13h shows a patient/user information screen, which allows for entering in information about the person that will be administered medicament.

Figure 13I:
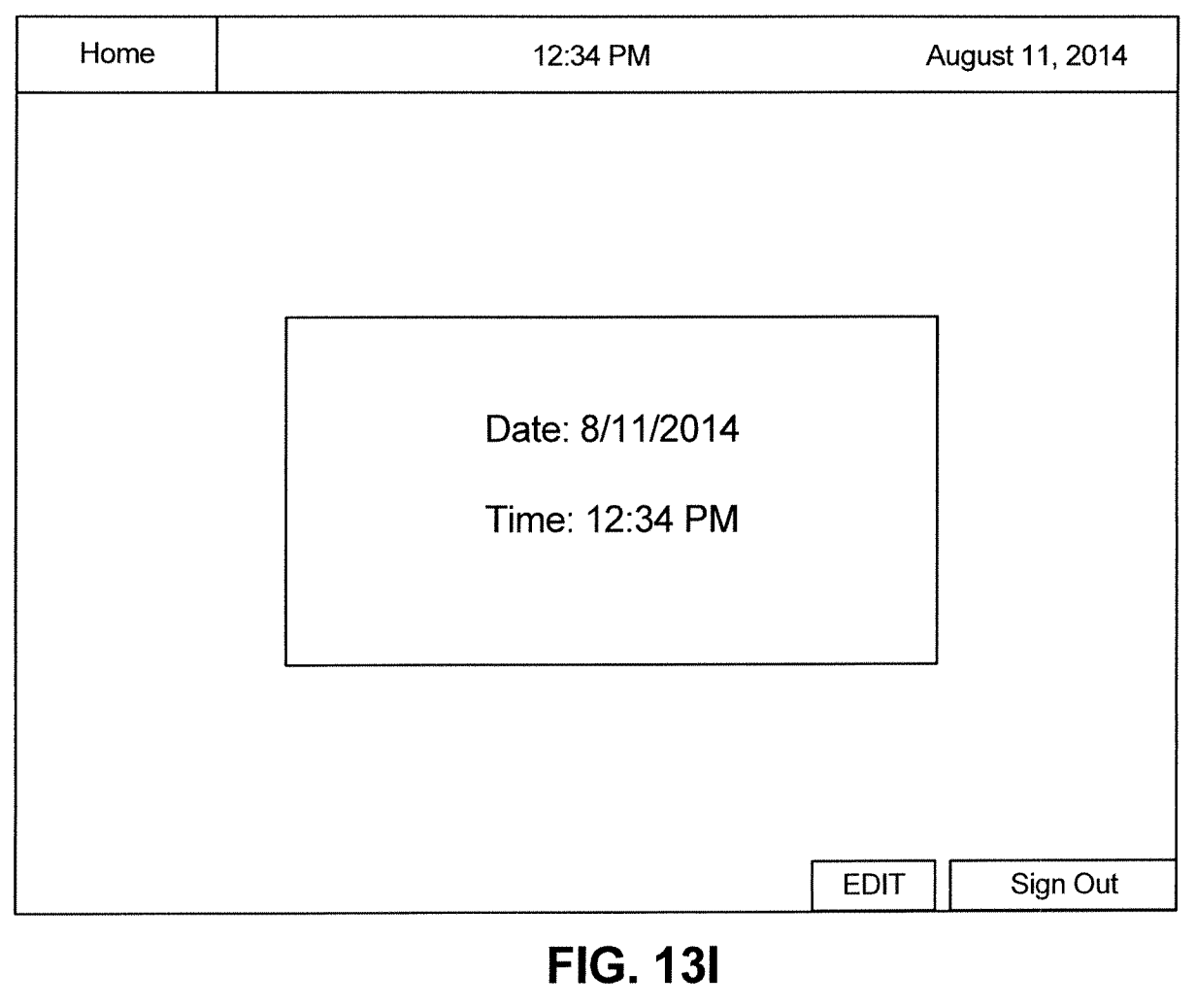

FIG. 13i shows a date and time screen, which allows the user to set the date and time; however, the date and time can be automatically set through a wireless connection.

Figure 13J:
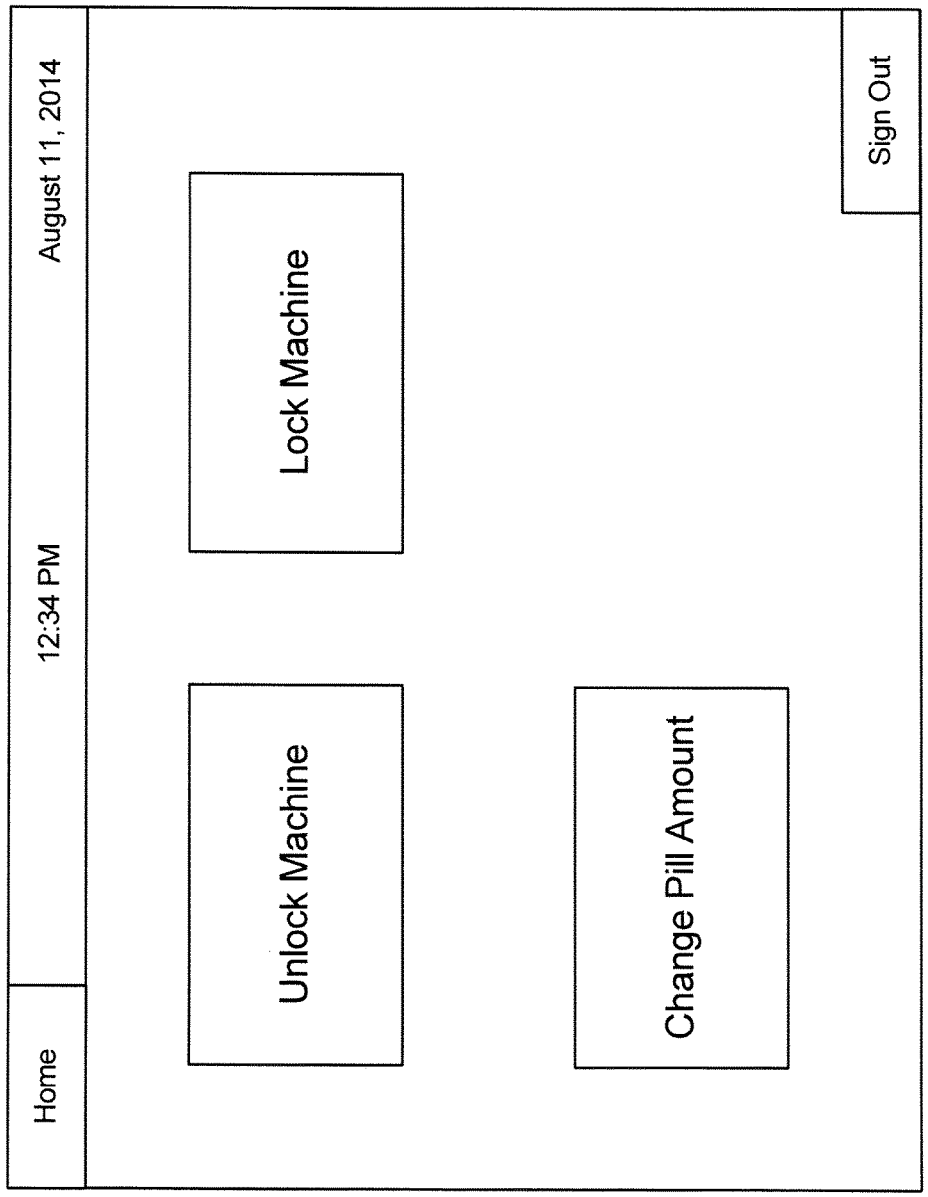

FIG. 13j shows a configuration screen that allows for locking and unlocking the device, and as well a tab to go to a screen that allows for configuring the medicament types, amounts, and frequencies of distribution.

FIG. 13k shows a log screen where the device tracks activity for tracking purposes.

Figure 13L:
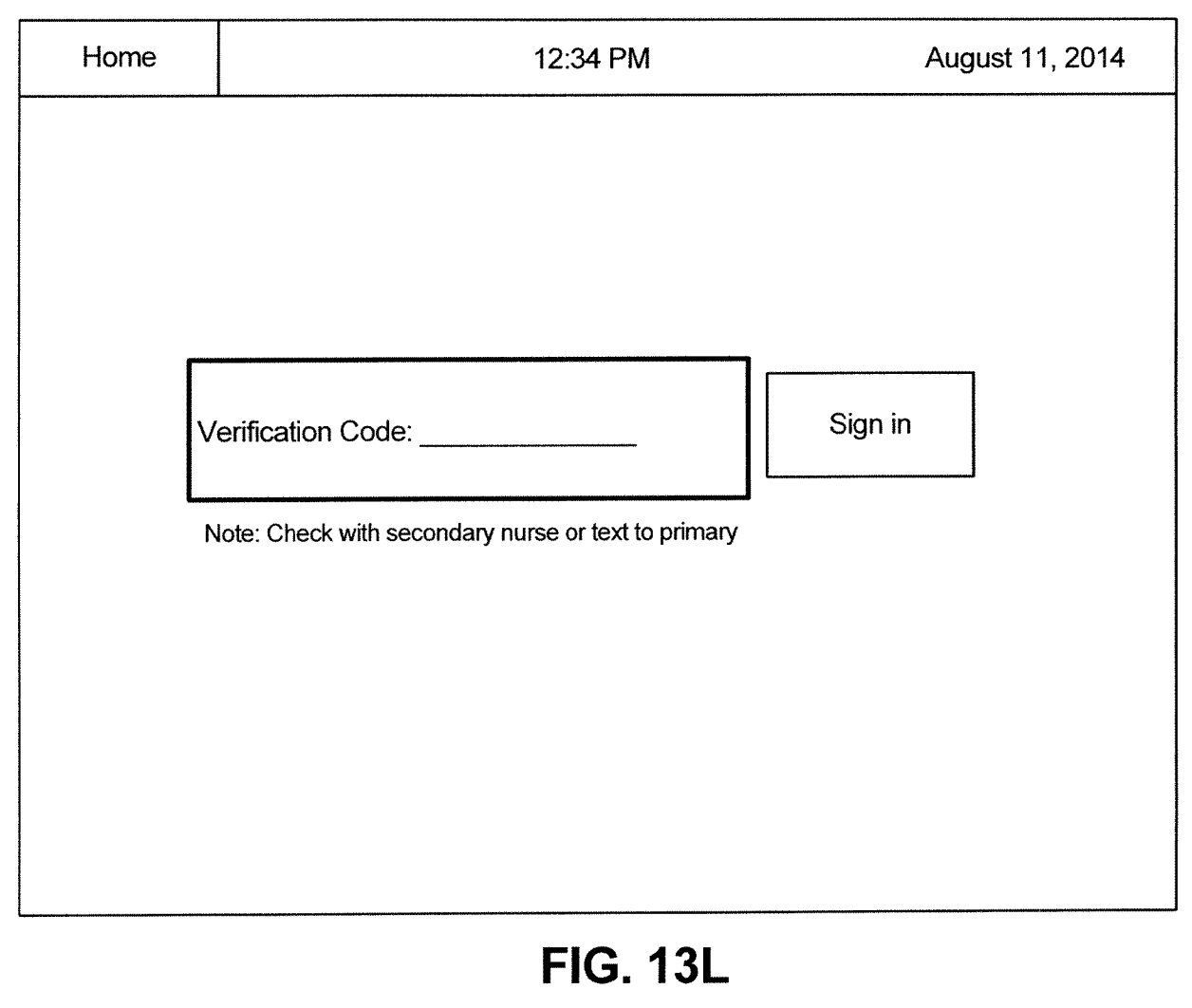

FIG. 13l shows a verification code screen, where a medical professional or person assigned to a user can monitor compliance.

Figure 13M:
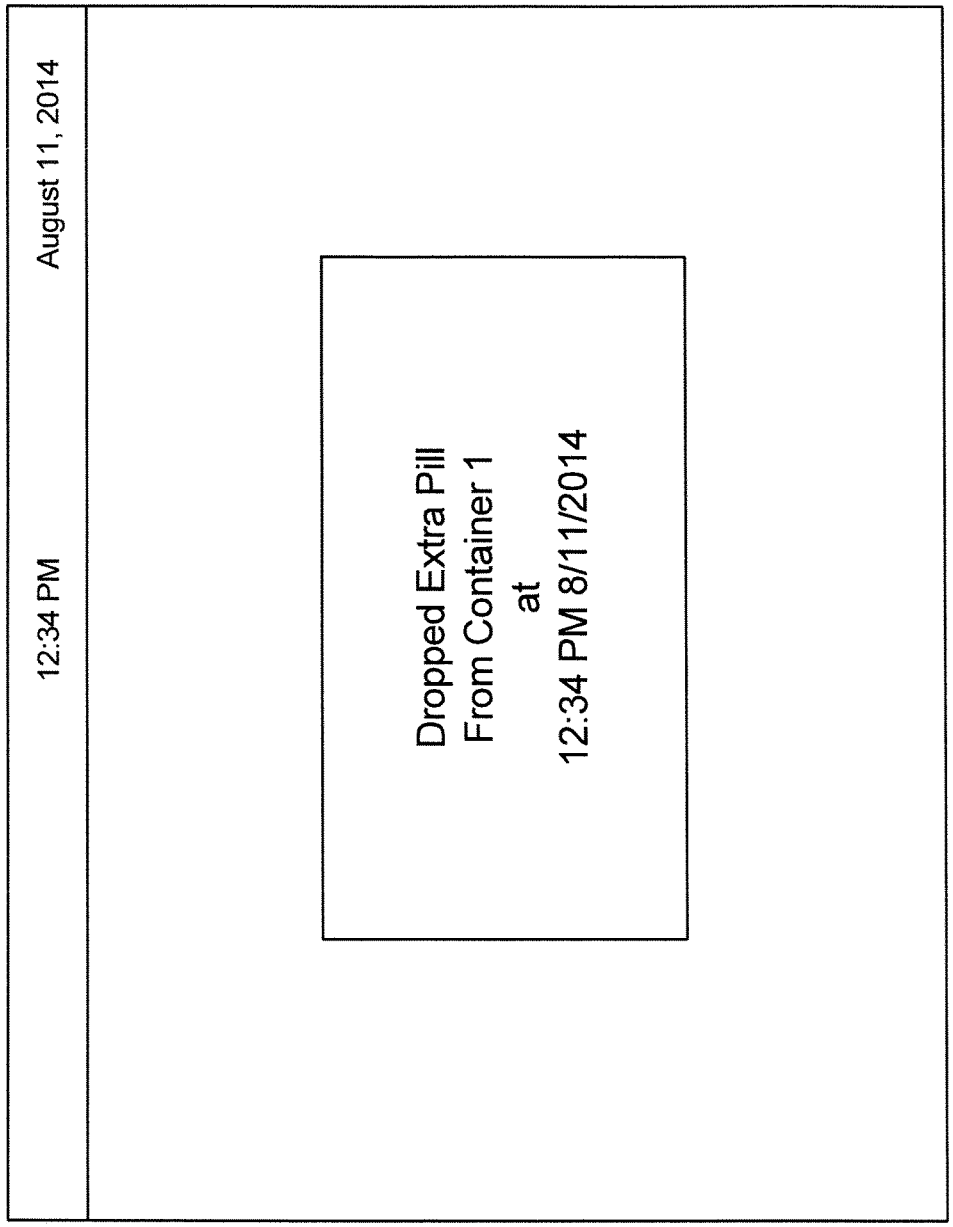

FIG. 13m shows an error screen, or a screen that can display particular acts of note.

FIG. 14 is a block diagram of the networked structure of the device. The device can communicate wireless with other devices. For example, the device can allow the user to access the device from a cell phone, or allow medical/pharmacy professionals to receive alerts or otherwise monitor in real-time the user's activities for emergency and/or compliance purposes.

It is to be understood that the foregoing descriptions and specific embodiments shown herein are merely illustrative of various embodiments of the invention and the principles thereof, and that modifications and additions may be easily made by those skilled in the art without departing for the spirit and scope of the invention, which is therefore understood to be limited only by the scope of the appended claims.

What is claimed is:

1. A system for compiling and dispensing a medicament to a user, comprising:
   a container;
   a sorting mechanism inside the container for controlled dispensing of doses of medicament, where a funnel shaped chamber comprising a series of narrowing spirals forms a choke point for the controlled release of medicaments; and
   a release device movable between a closed position where no medicament can be dispensed from the sorting mechanism and an open position where medicament can be dispensed from the sorting mechanism.

2. The invention of claim 1 further comprising a receptacle for receipt of the medicament from the release device and for presenting the medicament to a user.

3. The invention of claim 2 wherein the receptacle is located below the container.

4. The invention of claim 1 wherein the release device is located at the bottom of the sorting mechanism and the medicament is gravity fed from the sorting mechanism to the release device.

5. The invention of claim 4 wherein the release device comprises a tray located in a slot in the container having a hole, which when the hole aligns with the bottom of the sorting mechanism the release device is in the open position and when the hole is not aligned the release device is in a closed position.

6. The invention of claim 4 wherein the release device comprises a gear driven disc having a hole, which when the hole aligns with the bottom of the sorting mechanism the release device is in the open position and when the hole is not aligned the release device is in a closed position.

7. A system for sorting and dispensing individual does of a medicament to a user, comprising:
   a case;
   a frame inside the case;
   a plurality of containers for storing medicaments and comprising a gravity fed sorting mechanism for sorting between multiple doses of a medicament having a progressively narrowing spirals from top to bottom such that only one of the doses of medicament can pass through the bottom of the container; and
   a release device inside the containers movable between a closed position where no medicament can be dispensed from the sorting mechanism and an open position where medicament can be dispensed from the sorting mechanism.

8. The invention of claim 7 further comprising a receptacle for receipt of the medicament from the release device and for presenting the medicament to a user.

9. The invention of claim 8 wherein the release device comprises a device that can individually select between the plurality of containers.

10. The invention of claim 9 wherein the device comprises a rail with an actuator moving thereon and the actuator rotates a push rod to move between the open and closed position.

11. The invention of claim 7 further comprising a lid on the case.

12. The invention of claim 7 further comprising a lid on the plurality of containers.

13. The invention of claim 7 further comprising a computer control system of operating the system.

14. The invention of claim 7 further comprising a lockbox.

15. The invention of claim 13 wherein the computer control system has a network connection to receive and transmit information from and to other devices connected to the network.

16. The invention of claim 15 wherein the information is transmitted over the network to the device of a healthcare professional.

17. The invention of claim 15 wherein the computer system can provide a user with alerts as to the taking of the medicaments.

18. The invention of claim 7 where the release device further comprises a tray at the bottom of the containers where the tray can be moved between the open and closed position.

19. The invention of the claim 18 where the trays are moved between the open and closed position by a rod moving under the power of an actuator.

20. The invention of claim 19 where the actuator moves between the trays on a rail.

21. The invention of claim 20 where the narrowing spirals form a choke point for the controlled release of medicaments.

22. A system for sorting and dispensing does of a medicament to a user, comprising:
   a case;
   a frame inside the case;
   a plurality of containers;
   a sorting mechanism inside the containers for sorting and dispensing of doses of medicament that changes shaped from a first end to a second end that terminates in a choke point descending from progressively narrowing spirals thereby substantially conforming to the shape of a dose of medicament thereby allowing a single does to be dispensed at a time; and a release device inside the containers movable between a closed position where no medicament can be dispensed from the sorting mechanism and an open position where medicament can be dispensed from the sorting mechanism.

* * * * *